United States Patent [19]

Pankratov et al.

[11] Patent Number: 4,865,029

[45] Date of Patent: Sep. 12, 1989

[54] ENDOPHOTOCOAGULATION PROBE

[75] Inventors: Michail M. Pankratov, Waltham; Oleg Pomerantzeff, Brookline, both of Mass.

[73] Assignee: Eye Research Institute of Retina Foundation, Boston, Mass.

[21] Appl. No.: 36,959

[22] Filed: Apr. 16, 1987

Related U.S. Application Data

[63] Continuation-in-part of Ser. No. 856,045, Apr. 24, 1986, abandoned.

[51] Int. Cl.[4] .............................................. A61N 5/06
[52] U.S. Cl. ................................... 128/303.1; 128/398
[58] Field of Search ....................... 128/303.1, 395–398

[56] References Cited

U.S. PATENT DOCUMENTS

| | | | |
|---|---|---|---|
| 3,467,098 | 9/1969 | Ayres | 128/303.1 |
| 3,528,424 | 9/1970 | Ayres | 128/303.1 |
| 3,821,510 | 6/1974 | Munchenyan | 128/395 |
| 3,982,541 | 9/1976 | L'Esperance, Jr. | 128/303.1 |
| 4,076,018 | 2/1978 | Heckele | 128/6 |
| 4,228,341 | 10/1980 | Zindberg | 128/303.1 |
| 4,249,533 | 2/1981 | Komiya | 128/303.1 |
| 4,289,378 | 9/1981 | Remy et al. | 128/395 |
| 4,290,667 | 9/1981 | Chown | 350/96.18 |
| 4,316,467 | 2/1982 | Muckerheide | 128/303.1 |
| 4,421,382 | 12/1983 | Doi et al. | 128/303.15 |
| 4,475,788 | 10/1984 | Tamassini et al. | 350/96.18 |
| 4,494,540 | 1/1985 | Erb | 128/303.1 |
| 4,576,160 | 5/1986 | Tanaka | 128/303.1 |
| 4,718,417 | 1/1988 | Kittrell et al. | 128/303.1 |

FOREIGN PATENT DOCUMENTS

| | | | |
|---|---|---|---|
| 0152686 | 8/1985 | European Pat. Off. | 128/303.1 |
| 0215698 | 11/1984 | Fed. Rep. of Germany | 128/303.1 |
| 1557974 | 2/1969 | France | |

OTHER PUBLICATIONS

D. B. Karlin, "Intravitreal Argon and Carbon Dioxide Laser, and Xenon Arc Photocoagulation in Vitreoretinal Surgery", Graefe's Arch. Clin. Exp. Opthalmol. (1986) 224:221–225.

F. A. L'Esperance, Jr., "Ophthalmic Laser", Second Ed. Chapter 3 (1983), C. V. Mosby Co. publisher, pp. 28–84.

G. A. Peyman, et al, "Argon Endolaser", Arch. Ophthalmol., vol. 99, (Nov. 1981), pp. 2037–2038.

Primary Examiner—Lee S. Cohen
Assistant Examiner—David Shay
Attorney, Agent, or Firm—Lahive & Cockfield

[57] ABSTRACT

An endophotocoagulation probe has a probe tip adapted for insertion into the eye of a subject, and includes an optical fiber for carrying light, and a lens for focusing the light from the end of the fiber onto target tissue at a desired working distance. The lens forms a convergent beam with the waist of the beam providing a spot of maximum power density whose size is independent of the ocular medium. In a preferred embodiment a positioner provides selective variation of the spacing between the lens and the fiber to select a desired spot size. Preferably the lens is a selfocal or rod lens. A step-positioning handle selects one of a plurality of determined spacings, so as to achieve plural different spot sizes, each having a predetermined power density. Examples of probes having variable spot sizes in ranges from 50 to 500 microns are described with particular fibers and selfocal lens elements. A microprocessor may control lens position and light input power in accordance with the selected spot size. The operator may select a collimated, or different divergent or convergent beams, without withdrawing the instrument from the eye.

10 Claims, 9 Drawing Sheets

TABLE I

| SPOT SIZE RANGE | 50–100μ | 100–400μ | 300–500μ |
|---|---|---|---|
| FIBER OPTICS CORE (in μ)/N.A. | 25/0.11 | 50/0.10 | 200/0.13 |
| | 40/0.10 | 50/0.21 | 250/0.10 |
| | 50/0.10 | 100/0.10 | |

*FIG. 6*

TABLE 2

CALCULATED SPOT SIZE DIMENSIONS (μm) ON AND OFF TARGET

| WD (mm) | Displacement (mm) from WD | | | | | | | | |
|---|---|---|---|---|---|---|---|---|---|
| | -2.0 | -1.5 | -1.0 | -0.5 | 0 | +0.5 | +1.0 | +1.5 | +2.0 |

In vitreous

| WD (mm) | -2.0 | -1.5 | -1.0 | -0.5 | 0 | +0.5 | +1.0 | +1.5 | +2.0 |
|---|---|---|---|---|---|---|---|---|---|
| 3.990 | 350 | 287 | 225 | 162 | 100 | 197 | 293 | 390 | 487 |
| 5.449 | 294 | 258 | 222 | 186 | 150 | 220 | 290 | 360 | 431 |
| 6.912 | 290 | 268 | 245 | 223 | 200 | 254 | 308 | 363 | 417 |
| 8.367 | 309 | 294 | 279 | 265 | 250 | 296 | 344 | 390 | 437 |
| 9.826 | 338 | 328 | 319 | 309 | 300 | 342 | 383 | 425 | 467 |
| 12.744 | 411 | 408 | 405 | 403 | 400 | 436 | 471 | 507 | 542 |

In air

| WD (mm) | -2.0 | -1.5 | -1.0 | -0.5 | 0 | +0.5 | +1.0 | +1.5 | +2.0 |
|---|---|---|---|---|---|---|---|---|---|
| 3.000 | 432 | 349 | 266 | 183 | 100 | 229 | 357 | 486 | 614 |
| 4.097 | 341 | 293 | 245 | 198 | 150 | 243 | 337 | 430 | 523 |
| 5.194 | 320 | 290 | 260 | 230 | 200 | 272 | 344 | 416 | 489 |
| 6.291 | 328 | 309 | 289 | 270 | 250 | 312 | 374 | 437 | 499 |
| 7.388 | 350 | 337 | 325 | 312 | 300 | 356 | 411 | 467 | 522 |
| 9.582 | 415 | 411 | 407 | 404 | 400 | 447 | 495 | 542 | 589 |

*FIG. 7*

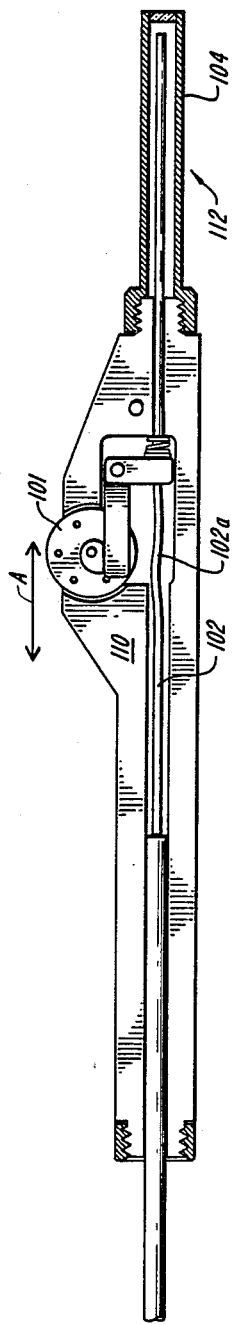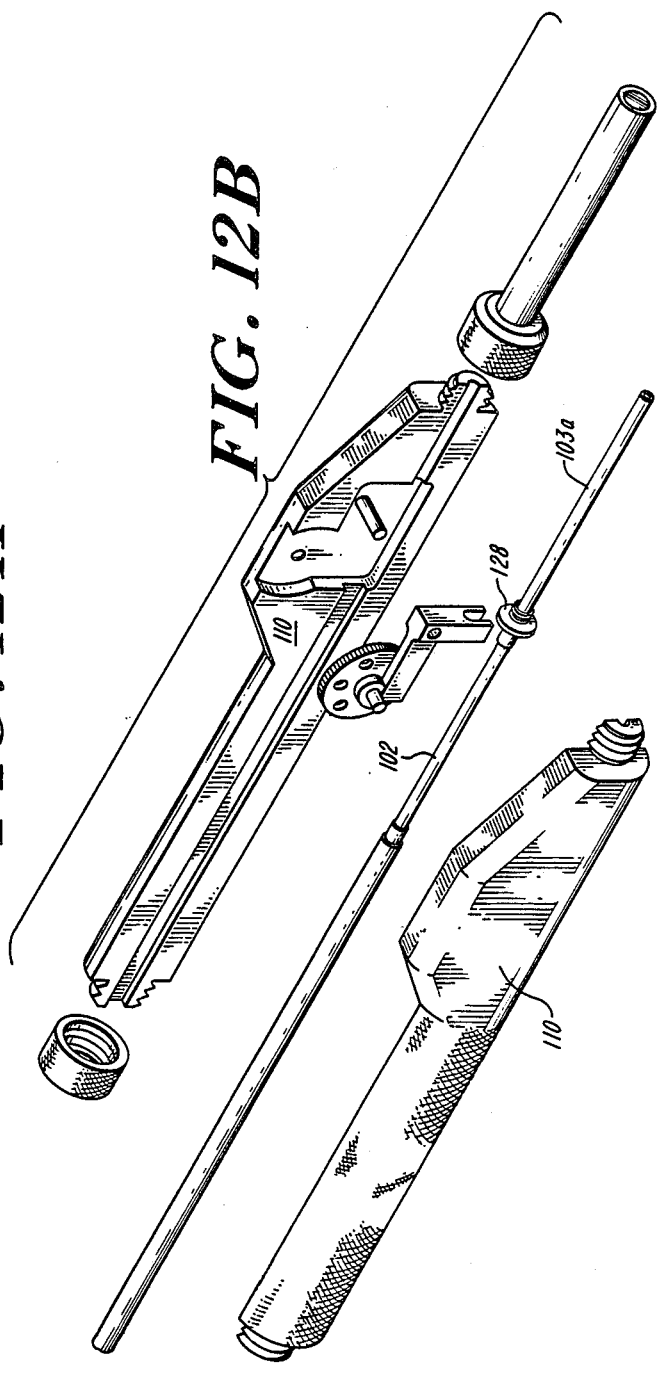
FIG. 12A
FIG. 12B

ENDOPHOTOCOAGULATION PROBE

This application is a continuation in part of Ser. No. 856,045 filed Apr. 24, 1986, now abandoned.

TECHNICAL FIELD

The present invention relates to a probe such as used for the surgical treatment of localized tissue areas by the application of high intensity light energy thereto. The invention also relates to endophotocoagulating probes, such as used for intracular phtocoagulation which may, for example, be performed at the time of pars planar vitrectomy.

Presently, known endophotocoagulation probes available to a surgeon have an optical system consisting essentially of a single quartz fiber of a selected diameter having a polished end. The fiber is encased in a thin, needle-like tube which is inserted into the eyeball through an incision in the cornea in order to treat tissue located, for example, at the eye fundus. High power light energy is applied at one end of the fiber and the other end delivers a divergent output beam. A surgeon using such a probe must estimate the beam diameter as projected onto the tissue, which depends on the divergence angle of the beam and on the distance between the fiber end and the target tissue. Since the divergence angle varies depending on the surrounding medium, the delivered power density at the target site is greater when the beam travels through a fluid filled cavity than through air.

Destruction of tissue occurs in the region of tissue illuminated by the beam. This illuminated region is referred to generally herein as the "spot" of the probe. Because the size of the illuminated region depends both on the surrounding medium and on the distance from the fiber to the treated tissue, the actual dosage delivered by a prior art endophotocoagulator is a matter of considerable variation, and requires estimation of these parameters by the surgeon. Thus, it is desirable to provide an endophotocoagulation probe having a beam which forms a well-defined spot.

OBJECTS AND SUMMARY OF THE INVENTION

It is an object of the invention to provide a photocoagulation probe having definite and known spot size and light intensity distribution.

It is another object of the invention to provide a photocoagulation probe having a distinctive output beam pattern for aiding the operator in positioning the probe.

It is another object of the invention to provide a photocoagulation probe having a spot size independent of the surrounding medium.

It is another object of the invention to provide a photocoagulation probe having plural operator selectable beam sizes or patterns.

These and other desired features are achieved in an endophotocoagulation probe having an optic fiber for channelling light, and a lens for focusing the light from the end of the fiber onto target tissue. The lens forms a convergent beam with the waist of the beam providing a spot of maximum power density at a defined working distance. In one preferred embodiment a positioner varies the spacing between the lens and the fiber to the spot size. Preferably the lens is a grin lens, formed of a segment of a rod having a graded index of refraction. A step positioning handle selectively adjusts the spacing to one of a plurality of discrete spacings, so as to achieve plural different spot sizes, each having a known power density. In one embodiment, a single probe provides six operator selectable spot sizes within a range from approximately 100 to 400 microns. Probes using preferred fiber and selfocal lens elements and having spot sizes from below 50 to above 500 microns allow precise treatment of tissue targets of arbitrary dimensions.

BRIEF DESCRIPTION OF THE DRAWINGS

These and other features of the invention will be understood by reference to the figures, in which

FIG. 6 is a table of optical fiber elements suitable for probes with different spot diameters;

FIG. 7 is a table of calculated cross sections of a beam of one embodiment the invention in focused and defocused positions.

FIG. 12A shows a plan view of a related embodiment with such a focussing assembly.

FIG. 12B shows an exploded view of a related embodiment with such a focus assembly.

DETAILED DESCRIPTION

An endophotocoagulation probe is a non-contact surgical instrument used within the eye for projecting a beam of intense light energy to destroy tissue in a relatively local area, e.g. an area having a cross section of a millimeter of less, which may for example be vascular tissue in the retina.

Such a probe is distinguished, for example, from a cauterization probe having a light output face which is brought into direct contact with the tissue to be destroyed. An endophotocoagulation probe operates at a distance from the target tissue, and applies light energy thereto at a power sufficient to cause local tissue destruction by coagulation or the like. For purposes of illustration below, the invention is discussed in relation to a preferred embodiment for ophthalmic use. The invention is not so limited, however, and it will be apparent to those skilled in the art that the invention includes probes of diverse construction for the treatment of other tissue areas of the body.

Figure 1:
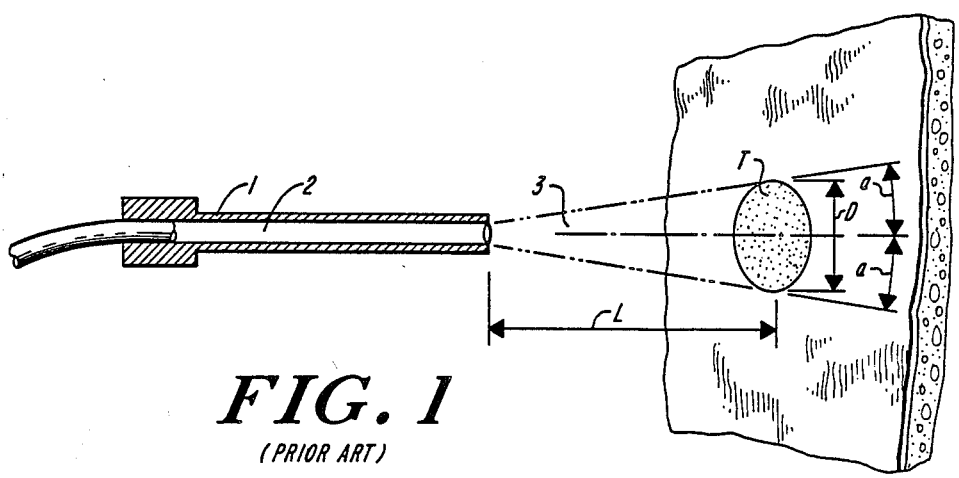
FIG. 1 is a schematic representation of a prior art endophotocoagulator and its beam pattern.

The essential elements of a prior art endophotocoagulation probe are shown in FIG. 1, and include a handle or frame member 1 mounting an optical fiber 2 therein. Member 1 includes a rigid sheath-like probe tip surrounding the fiber 2. High intensity light, e.g., from a laser source (not shown), is provided to a first end of the optical fiber, and emerges from the opposing end as a divergent beam 3. As shown, the angle of divergence "a" of the beam is narrow. The handle permits the manipulation of the fiber by a surgeon or other user so as to position its end face at a desired distance, denoted L in FIG. 1, from the tissue to be treated. The beam illuminates a target region T having a diameter D on the tissue. The high intensity illumination destroys tissue within the target region.

Because the output beam is divergent, the diameter of the region T varies directly with the distance L to the tissue. The power density in region T varies inversely with the square of the distance. The angle of divergence is different when the probe is used within a fluid medium such as vitreous humor, and when it is used in air, so the working medium is to be taken into consideration when computing the actual power reaching the tissue. Ideally, a surgeon using such a probe is to estimate the diameter of region T and the fiber-to-tissue distance accurately, because the inverse square intensity relationship can result in undesired perforations, scarring or deep tissue damage if the probe is brought too close to the layer of tissue to be treated. Working with a hand-held probe at millimeter or submillimeter range, these parameters are difficult to estimate, and instances of inadvertent tissue damage have been reported in the literature. Despite these shortcomings, the development of a simple ranging or optical positioning system for such a probe has proven elusive. This may be in part because the diameter of the fiber and holder, which for an ophthalmic probe may together amount to under one millimeter, precludes or discourages inclusion of conventional optical elements for ranging, positioning, or beam-collimating.

Figure 2:
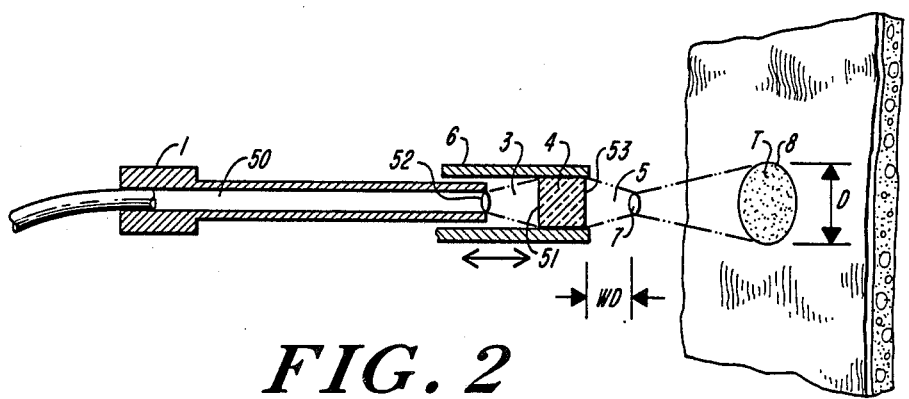
FIG. 2 is a schematic representation showing elements of a probe according to the invention and an illustrative coagulation beam pattern.

FIG. 2 is a schematic representation showing elements of a probe according to the present invention, and representative coagulation beam pattern. The fiber element 50 and the illuminated region T of diameter D correspond to the similar elements of FIG. 1. The present invention, however, also includes a focusing assembly which includes a lens 4 closely spaced from, and in optical alignment with, the output end 52 of the fiber 50 for forming a convergent output beam 5. Lens 4 is spaced from fiber 50 by a holder or positioner 6. As shown, the output beam 3 diverges from the end 52 of fiber 50 and strikes input face 51 of lens 4. The focusing assembly converts beam 3 to a convergent beam 5 of conical shape, which is emitted from output face 53 of lens 4 and converges to a narrow waist 7 at a definite distance, denoted the working distance WD, from the end of the probe. In the schematic representation of FIG. 2, holder 6 is a tubular member having lens 4 centrally mounted therein. Holder 6 is coaxial with fiber 50, and is adapted for motion along the axis of the fiber so as to position lens 4 a variable distance from end face 52 thereof. Each position of lens 4 from the end of face 52 of the fiber determines a different focal position and size of waist 7 of the convergent output beam 5. FIG. 2 shows beam 5 illuminating a region 8 of tissue. Because the plane of the tissue is not at the waist 7, region 8 is of larger diameter than the waist.

In accordance with the invention, waist 7, which is a cross section of maximum intensity, is brought into alignment with the target region of tissue. The waist is a well-defined "spot", which may be recognized by simple inspection of the beam. Accordingly, throughout this disclosure and in the claims, the word "spot" is used to refer to the waist of a convergent probe output beam, and also to refer to the illuminated region formed by such a beam on target tissue.

Thus, an endophotocoagulation probe according to the present invention includes a lens for forming a convergent treatment beam which converges to a spot of maximum intensity at a particular distance from the probe. According to a further embodiment, the spacing between the fiber end and the lens are adjusted to any one of several discrete selected distances to achieve selected different spot sizes at corresponding different working distances between the probe and the spot. According to a further embodiment, a collimated or a divergent beam is produced at additional discrete fiber - lens spacings of the same instrument.

Figure 3:
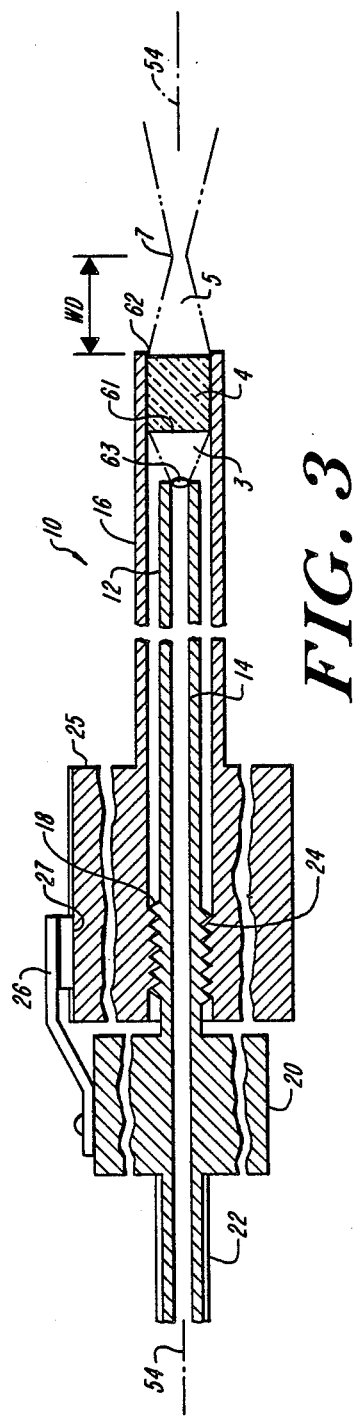
FIG. 3 is a schematic cross section along the axis of one embodiment of a step-zoom probe according to the invention.
Figure 3A:
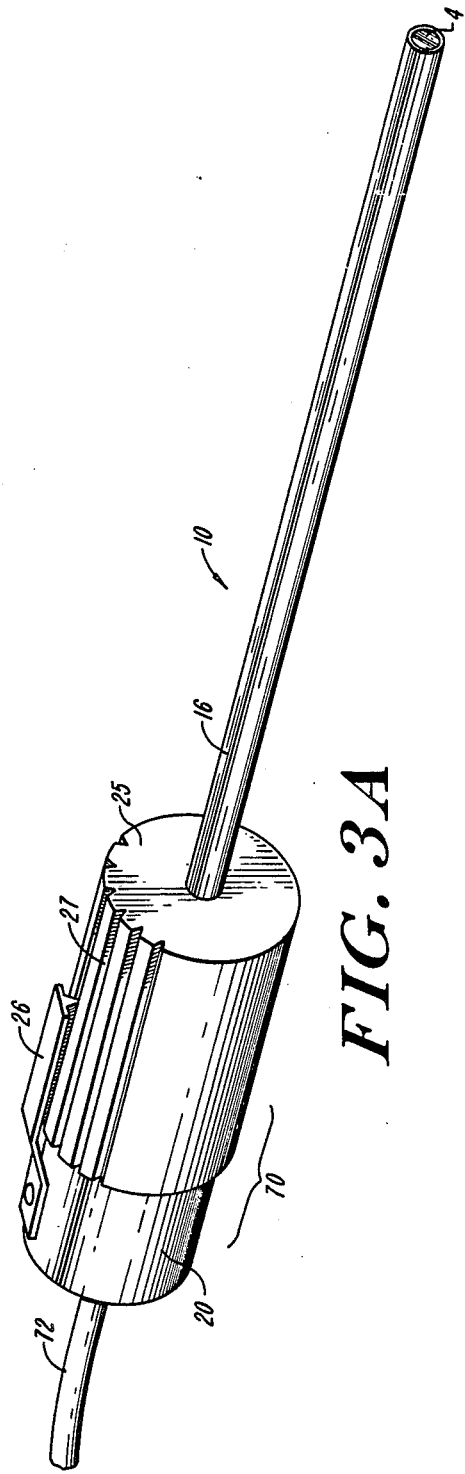
FIG. 3A is a perspective view of the device of FIG. 3.

One prototype embodiment 10 of such a probe is shown in FIGS. 3, 3A. This embodiment is referred to herein as a step-zoom probe FIG. 3 shows a schematic cross-section along the central axis 54 of the probe. Probe 10 includes a first tube element 12 encasing an optical fiber 14 and a second tube element 16 securing a lens 4 spaced in front of the fiber output end. Tube 16 may, by way of example, be thin-walled 20 gauge stainless steel tubing. The inner diameter of tube 12 may be up to 500 microns or more, depending on the diameter of the fiber 14 used therein. In this embodiment, tube 12 extends along the fiber axis to a shank having a threaded portion 18 for positioning the tube, and a handle portion 20. At an outer end of the handle portion 20, a protective jacket 22 connects to the tube and leads the input end of fiber 14 to a high power light source, such as a gas laser.

The outer tube 16 is mounted coaxially with the inner tube and carries at one end thereof, a lens 4 having an input face 61 and output face 62. At the opposite end, tube 16 extends to a knob 25 with a threaded portion 24 mating with threaded portion 18 of the inner tube. Rotation of the knob 25 with respect to the handle 20 rotates the mating threaded portions, causing relative motion of the two tubes along their common axis, thereby changing the axial spacing of the lens input face 61 and the fiber output face 63. A spring-loaded stop member 26 is mounted on handle 20 and positioned under spring tension to engage indentations 27 in knob 25 so as to define particular rotational positions of handle 20 and knob 25. Each rotational position thus determines a spacing between lens 4 and fiber end face 53, so that by manually rotating knob 25, a user selects different predetermined lens spacings, hence spot sizes of the probe.

The foregoing construction achieves an adaptable mechanical configuration for assuring that a coagulating beam has both a well-defined working distance, and, due to its fixed geometry, a spot of known power density at that distance.

The focal length of the lens 4 is preferably selected to provide a desired smallest spot size in conjunction with a fiber spaced a selected largest distance away from its input end. The largest distance WD is defined by a stop which determines a maximum relative rotation of the handle and knob. The smallest spot size in the range then has the shortest corresponding working distance and the greatest power density. All other spots are obtained by turning the handle to decrease the separation of the output end of the fiber from the input surface of the lens. As the fiber end "zooms" toward the lens, it generates a sequence of spots of progressively increasing size, formed at progressively greater distances from the lens, and each having corresponding lower power density. For each fiber to lens spacing, the image of the fiber end formed by the lens occurs at the position of the smallest cross-section of the exit beam. Preferably, all fiber to lens spacings are selected so that the output beam 3 of the fiber does not over-fill the lens, thus resulting in 100% transmission of the light power to the spot.

In the preferred step-zoom probe shown in FIG. 3, the spring-loaded stop arrangement is configured to provide six different spacings of the fiber and the lens, yielding six different size spots of known dimensions, distinct working distance and relative power density. BY relative power density is meant the (constant) ratio of the power density of a spot to the power density, e.g., of the smallest spot of the series, or of the fiber end output.

FIG. 3A shows a perspective view of the probe 10 of FIG. 3. As shown, the device comprises a handle portion 70, with a flexible connector 72 which may, for example, include a light delivery conduit. For alternative embodiments discussed below, connector 72 may further include electrical conductors for carrying position indicating or position controlling signals. Handle 70 includes portions 20, 25, one of which is connected to a tubular member 16 holding the lens 40. Indentations 27 are at spaced-apart rotational positions about handle portion 25, with the spacing calculated to yield the desired spot sizes.

Figure 10:
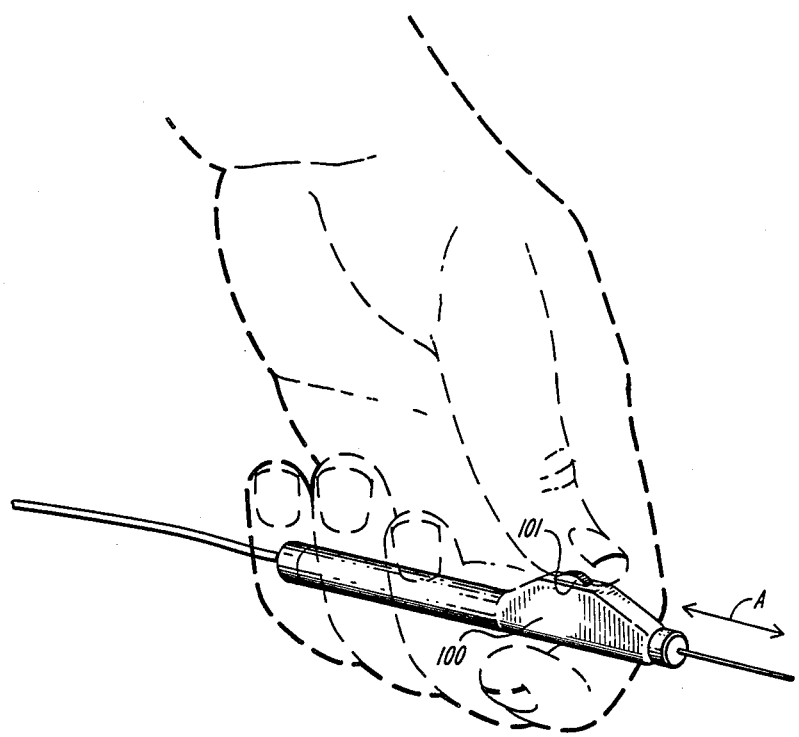
FIG. 10 shows a perspective view of a presently preferred prototype instrument according to the invention.

FIG. 10 shows a perspective view of a presently preferred embodiment of a step zoom endophotocoagulation probe 100 according to the invention. In this embodiment, a thumbwheel 101 is coupled to an internal mechanism for varying the fiber-lens spacing. The thumbwheel itself is rotated by tangential motion directed along the axis "A" of the instrument, resulting in enhanced stability and operator control. Details of the focusing mechanism, and alternative embodiments thereof are discussed below in connection with FIGS. 11, 12A and 12B.

Figure 11:
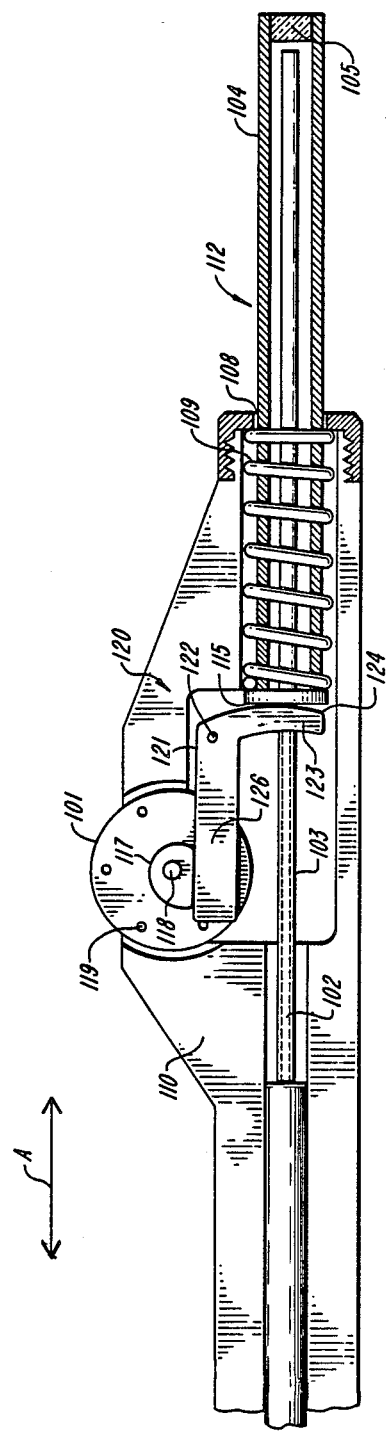
FIG. 11 shows a cutaway side view of an embodiment similar to that of FIG. 10 with a preferred focusing assembly.

FIG. 11 shows a partial view of an embodiment of a focusing endophotocoagulation probe 100 according to the invention, which is illustrative of a presently preferred focusing design. Probe 100 has a handle 110 and a tip portion 112 of dimensions comparable to the probe of FIGS. 3, 3A and to the fixed endoprobes of the prior art. Probe 100 differs from the probe of FIGS. 3, 3A, however, in having a focusing mechanism wherein a focusing thumbwheel 101 is rotated by motion along the axis of the fiber, denoted, "A", to vary the fiber to lens spacing. Applicant has found that such axial adjustment motion provides excellent operator control while not interfering with the aiming of the beam at a target tissue.

As shown in FIG. 11, handle 110 secures a light conducting fiber 102 and its surrounding inner sheath 103 in a fixed position. An outer sheath or tube 104 (corresponding to tube 16 of FIG. 3) holds a rod lens 105, and coaxially surrounds the fiber's sheath 103. Tube 104 extends through an opening 108 in the front part of handle 110, and is biased by a compression spring 109 into a retraction position determined by a stop-defining generally L-shaped yoke assembly 120.

Yoke assembly 120 includes a pivoting member 121 which pivots about a pin 122 in the handle. A first end 123 of the yoke assembly is a yoke-like fork which fits about the inner sheath 103 and has a curved contact face 124 which presses against a thrust face 115 of the end of tube 104 to move tube 104 axially against the force of spring 109, thus varying the spacing between the tip of fiber 102 and lens 105. A second end 126 of the yoke assembly bears against a cam surface 117. Cam 117 is coaxially attached to thumbwheel 101 to pivot about a second pin 118 in the handle. Cam surface 117 may be a generally rounded polygonal surface with a plurality of sides each spaced at a different distance from pivot 118, so as to each define a different discrete position of yoke end 126, and thereby an axial position of tube 104. Alternatively, cam 117 may comprise a continuously varying cam surface, with particular desired spacings determined by a number of preset rotational detents 119 in the thumbwheel assembly. In use, the operator rotates thumbwheel 101 to vary the fiber to lens spacing, thereby selecting a desired spot size.

FIGS. 12A, 12B show another step-position mechanism for the embodiment of FIG. 10. This embodiment has a cam driven yoke assembly 120 like that of FIG. 11, but has a fixed outer tip assembly 112. In the embodiment of FIG. 12A, 12B, however, yoke member 121 bears against a collar 128 affixed to a rigid tube 103a holding fiber 102, and thus moves the fiber back and forth relative to a rigidly positioned lens 105 in fixed tip 112. As best seen in FIG. 12A, the fiber 102 has a portion 102a which is not rigidly sheathed, and which is loosely suspended in a portion of the handle so that it may move slightly, as the instrument is focused, without stretching or otherwise stressing the fiber.

In related embodiments, other mechanisms for positioning the lens may be used. For example, a rack and pinion mechanism, or a linear frictional drive may be used to provide the required displacement of tubes 103 or 104, or a combination of rotation-reducing gearing and linear displacement coupling elements may be used. The mounting structure may be varied to make the outer tube 104 fixedly coupled to the handle, and the inner fiber-bearing tube 103 spring mounted for motion within the handle, or vice-versa.

In a further preferred embodiment, a step zoom endoprobe according to the invention is fabricated as a disposable assembly with at least the handle and positioning assembly, and preferably also one or more tubes 103, 104 and other parts formed of molded plastic components. Such a device may be inexpensively produced and provided as a sterilized unit for single operation use, thus eliminating the need to disassemble and sterilize the surgical tool after each use. Such a single-use disposable embodiment may be implemented with a movable inner tube, as discussed above, without considering the long-term effects of fiber stress caused by movement, thus permitting the outer tube to be permanently and immovably sealed to (or formed with) the handle. This latter construction eliminates openings to the interior of the handle, such as opening 108 shown of FIG. 10, enhancing the sterilization processing of the implement.

In the discussion of embodiments above, frequent reference is made to a fiber-to-lens spacing for providing a convergently focused spot which is an image of the fiber output end. It is also possible with applicant's structure to provide a stop which defines an axial position of the fiber end at the lens focal point, or at a position closer to the lens than its focal point. These two fiber-lens spacings yield a collimated or a divergent output beam, respectively. In contrast to the sub-millimeter displacement for providing convergent step-zoom spots, somewhat larger total displacement is necessary to include a collimated or a divergent beam forming spacing. In further embodiments of a probe according to the invention, the variable positioning thumbwheel is adapted to provide, in addition to one or more convergently focused spots, a collimated or a divergent output beam, or both. In this manner, a single instrument provides both fine focused spot sizes suitable for microsurgery upon targets near to the macula, and a collimated, or a conventional diverging beam having an effective spot size at the target of approximately one to three millimeters.

In further embodiments of the invention, it is envisaged that by replacing the single fiber 102 with a fiber bundle, or with a specially fabricated coaxially mounted fiber, having inner and outer light conducting regions, the spot size may be varied with a fixed lens spacing by turning on or off one or more radially outer fibers. Such embodiments have the advantage of allowing motionless, external, electronic control of spot size during surgery, with each spot formed at the same focal distance from the probe. For such embodiments, the term "fiber" as used in this description and the appended claims, shall be understood to include a fiber having plural distinct radially-spaced light conducting portions, or a fiber bundle having such spatial fiber distribution.

Various design considerations and technical details are set forth below, illustrating the performance range of an endoprobe constructed according to the invention.

According to the illustrated prototype embodiments of the invention, the lens or focusing element is a positive self-focusing lens of the type sold under the SELFOC trademark. Such lenses are characterized in having a graded index of refraction which is rotationally symmetric about a central axis and radially variable, with highest refractive index on the axis and decreasing index toward the periphery. One suitable material for making such lenses is rod stock manufactured by Nippon Sheet Glass Co, Ltd., of Osaka, Japan, and is sold under their SELFOC trademark as positive GRIN rod stock. A GRIN rod has the useful optical characteristic of bending incident light rays in a wave-like fashion so that the light travels in a sinusoidal path with a period of oscillation P, called its pitch, which depends only on the axial refractive index and the wavelength of the light. This property permits the use of a rod segment of short axial length as the lens 4, as shown in FIG. 3.

Figure 4A:
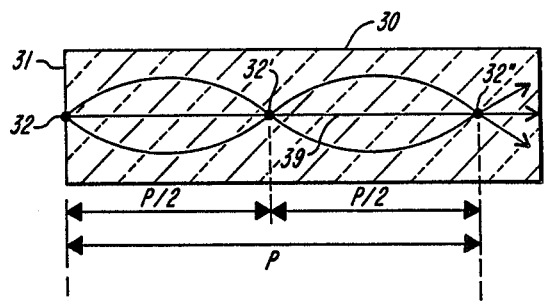
FIG. 4A illustrates the path of light beams entering at the point of highest index of refraction in a GRIN lens.

Several dimensional and optical design factors related to the use of such a lens in the present invention will be understood with reference to FIGS. 4A, 4B, 5A and 5B. FIG. 4A shows a cross-section of a GRIN rod 30, having a central longitudinal axis 39, and traces ray paths for an object point 32 lying on end face 31 of the rod on the central axis. As shown, rays from point 32 on the axis are imaged at successive image points 32', 32' on the axis at distances P/2, P along the axis.

Figure 4B:
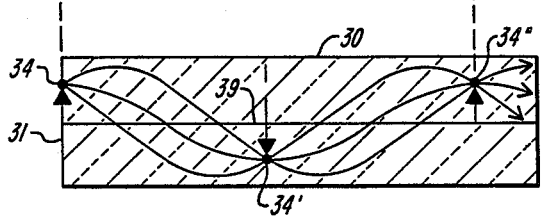
FIG. 4B illustrates the path of light beams entering at a point of lower index of refraction in a GRIN lens.

FIG. 4B shows an identical cross section of a GRIN rod lens 30 and a point 34 lying on end face 31 but located off the central axis of the rod. As shown, off-axis point 34 is imaged at image point 34' located at a distance P/2 along the axis, in inverted orientation. At distance P, point 34 is re-imaged at point 34'', in proper orientation and with unit magnification. As noted above, distance P is called the pitch of the rod lens, and is a characteristic of the refractive index. According to the preferred embodiment of the invention, as shown in FIG. 3, a segment of a positive GRIN rod having a length lying between $(nP/2)$ and $((n+1)P/2)$, where n is a small integer, serves as a lens element for focusing light.

Figure 5A:
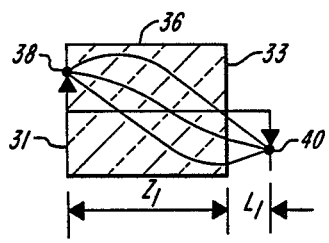
FIG. 5A illustrates the path of light rays entering a GRIN lens of smaller length at a point of lower index of refraction.
Figure 5B:
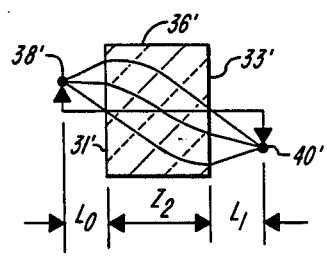
FIG. 5B illustrates ray paths for light from an object entering the lens.

FIGS. 5A, B show imaging properties of positive GRIN rod lenses 36, 36' of length shorter than P/2. FIG. 5A is a schematic sectional view of a lens 36 having a length $Z_1 < P/2$ imaging an object point 38 located on its input end 31. This arrangement corresponds to lens 4 of FIG. 3 when there is no air separation between the end of the optic fiber 14 and the lens. In this case, object point 38 on the input surface of the rod lens is imaged at image point 40 located a distance $L_1$ outside of output face 33 the lens. FIG. 5B shows another rod lens 36' of length $Z_2 < P/2$, used to image an object point 38' situated a distance $L_0$ away from the input face 31 of the lens 36'. This situation corresponds to the fiber/lens arrangement of FIG. 3 with the fiber end separated from the lens by a distance $L_o$. In this case, the length $Z_2$ of lens 36' can be chosen such that the image of object point 38' focuses at image point 40' located a distance $L_1$ from the output face 33' of the rod. Thus, by suitably choosing the length of a segment of a GRIN rod, one can arrange it so that the rod focuses the light originating at or near its input face into a focal region a desired working distance $L_1$ away from its output face. As with a conventional lens, motion of the object 38' towards input face 31' results in the formed image 40' receding from the input face 33', resulting in a larger working distance.

It will be understood that although the foregoing discussion relates to FIGS. 5A,B showing a lens of length Z (that is, $Z_1$ or $Z_2$) shorter than P/2, a lens of length $(Z + np/2)$ for (n) an integer, will also focus the image a distance $L_1$ from it output face. The image will be inverted for (n) even, and will suffer progressive but moderate transmission loss for increasing (n). For ease of handling, it may be desirable to use GRIN rod lenses of length Z, $(Z + P/2)$, $(Z + P)$ or other low integral increment of $(P/2)$. Accordingly, when it is specified herein and in the claims that the length is "less than a half-pitch", that term includes a length that is less than a multiple of a half-pitch. The relevant limitation is that the rod be of such a length as to function as an optical lens.

It has been found that the foregoing focusing property of positive GRIN rods is well suited for their use as lens elements to achieve a spot of determined size and focal position in an endophotocoagulation probe. Various details related to their use in probes such as the embodiment shown in the figures will now be discussed by way of illustration.

FIG. 6 is a table identifying commonly available optical fibers suitable for conducting laser light to form spots in various size ranges when used in conjunction with a GRIN rod lens. For a given fiber, one determines the desired focal length of a GRIN rod which optimally provide the spot range indicated with minimal power transmission loss. As shown, fibers having a light transmissive core diameter, exclusive of cladding, between approximately 25 and 50 microns and a numerical aperture of approximately 0.1 may be used for a step-zoom probe covering the spot diameter range of 50 to 100 microns. At the high end, fibers having a 200–250 micron core diameter can be used for forming 300–500 micron spots. Three probes of different sizes each having a single such fiber as its light conductive element can cover a range of spot sizes from 50–500 microns, at convenient working distances and with negligible transmission losses. Those skilled in the art will understand from this description that larger or smaller spot probes may also be so constructed.

FIG. 7 shows a table of calculated cross-sections of the output beam waist of a test probe employing a 50 micron core diameter, 0.21 NA fiber using argon green 514.5 nm light and a particular GRIN rod lens, 700 microns in diameter, described more fully below. Design calculations were carried out to obtain spot sizes of 100, 150, 200, 250, 300 and 400 microns at the waist of the probe output beam. The waist for each spot size occurs at the working distance (WD) appearing in the left hand column of the table. Calculations were carried out for a medium containing either vitreous humor or air, to determine the spot size which would be formed on tissue if the lens were axially displaced by up to two millimeters in either direction from the nominal focal position WD. As noted above, the spot size remains constant independently of whether air or vitreous humor is the interstitial medium; only the working distance shifts due to the steeper convergence angle of the output beam when light refracts at the lens/air interface.

Of particular note in FIG. 7 is the extreme dependence of spot size on axial position for the smaller spot sizes. Thus, for example, with a 100 micron "spot" or focal waist of the convergent beam, a translation of the probe by one millimeter along the axis results in spot broadening in vitreous by a factor of 3.21 (in the minus direction) to 4.42 (in the positive direction), and between 2.66 and 3.57 in air. Since the spot power density is inversely proportional to the square of these factors, it can be seen that the illuminating power quickly drops to a level of 10% or less when a probe is in a defocused position. Similar but less extreme effects hold for the larger diameter spot sizes.

Figure 8B:
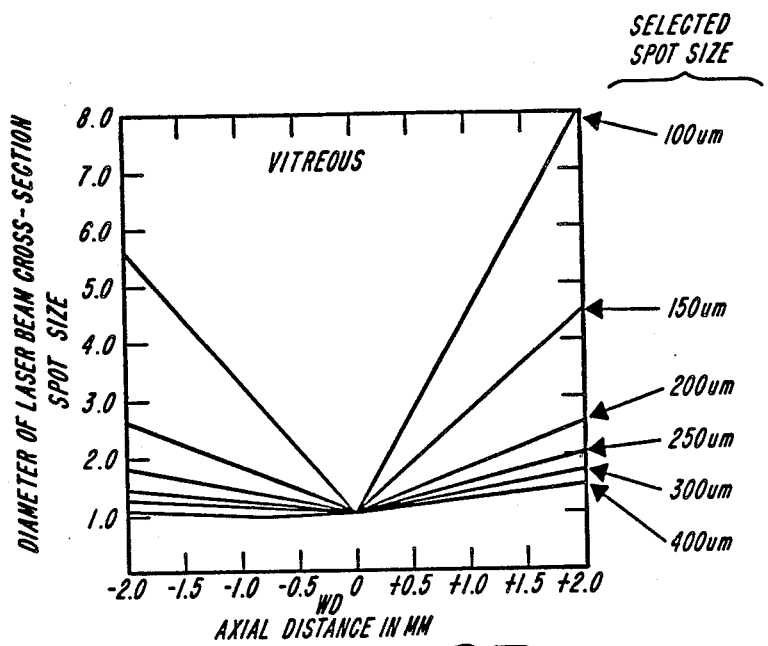
FIG. 8B shows the normalized variations of spot diameter for the probe of FIG. 7 in air.
Figure 8A:
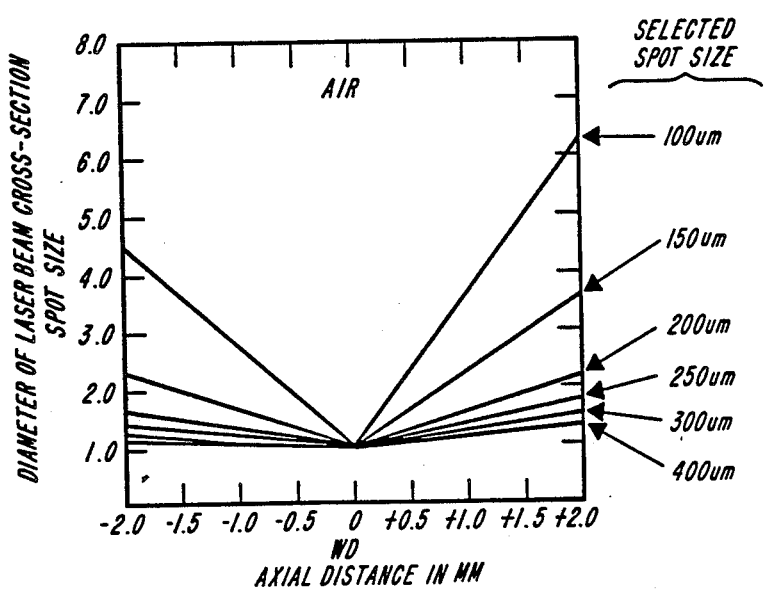
FIG. 8A shows the normalized variations of spot diameter for the probe of FIG. 7 in vitreous.

FIGS. 8A and B show the normalized variation of spot diameter in air and in vitreous, respectively, when the probe is in a defocused position. These Figures graphically illustrate the functional dependence of spot dispersion upon axial motion of the probe. In particular, with the smaller spot sizes (e.g., below 250 microns) the variation in spot diameter with axial motion of the probe is so pronounced that it essentially eliminates the possibility of damage to tissue away from the focal region. Even with larger spot sizes, dropoff of the power density in defocused positions is achieved. Also, using a probe having such a beam pattern, a surgeon may position the probe at the correct working distance by visual inspection. The surgeon need only move it slightly back and forth, using low power illumination, and observe the consequent spot expansion and contraction until the correct working distance is obtained. Thus, the greater dropoff characteristics correspond to a highly convergent pattern which allows precise visual determination of proper placement of the probe at the required working distance. This capability reduces dosage errors caused by incorrect positioning.

Dimensions and technical properties of elements of one representative probe will now be described in detail by way of example. Other examples for probes having a different range of spot sizes may readily be calculated by a person skilled in the art.

In the illustrative embodiments of FIG. 10 and FIGS. 3, 3A, fiber 14 was a quartz fiber having a 50 micron core diameter, 0.21 NA and an index of refraction of approximately 1.46. The output beam from such a fiber diverges in the air-filled fiber/lens interspace at an angle of approximately 12° from the fiber axis. Lens 4 was a segment of positive GRIN rod identified by its manufacturer, Nippon Sheet Glass Co, Ltd., as the ISLW series. Lens 4 had a diameter of 700 microns, was a quartz rod enriched by surface diffusion so as to achieve a refractive index tapering from 1.648 at its core to 1.610 at its periphery. Lens 4 was formed of rod stock mounted in a 20 gauge stainless steel tube. It had a nominal pitch of 7.7 mm for 514.5 nm light, and was cut in a segment approximately 4.72 mm long. This intermediate length, greater that a half-pitch and less than a full pitch length, was chosen for ease of handling. The smallest spot was a 100 micron spot, and was achieved by positioning the output end of fiber 14 a distance of 1.354 millimeters from the input face of the lens. With this geometry, a working distance of 3 millimeters between the output beam waist and the output face of the lens was obtained. Stops in the threaded handle were arranged to provide positive detents at fiber-lens spacings of 1.354, 1.172, 1.080, 1.026, 0.989, and 0.942 millimeters, resulting in spot sizes of 100, 150, 200, 250, 300, and 400 microns, respectively. The corresponding working distances, varying from approximately 3 to approximately 10 millimeters in air and vitreous, are set forth in the left hand column of table 2, FIG. 7.

It will be apparent that the mechanical structure of the step-zoom probe has been described by way of illustration only. Rather than the hand-moved threaded collar with a detent structure illustrated in FIGS. 3, 3A, an electronic micropositioning motor, such as a stepping motor, connected to a screw or to a linear drive, may be provided for varying the spacing of the fiber and the lens.

Figure 9:
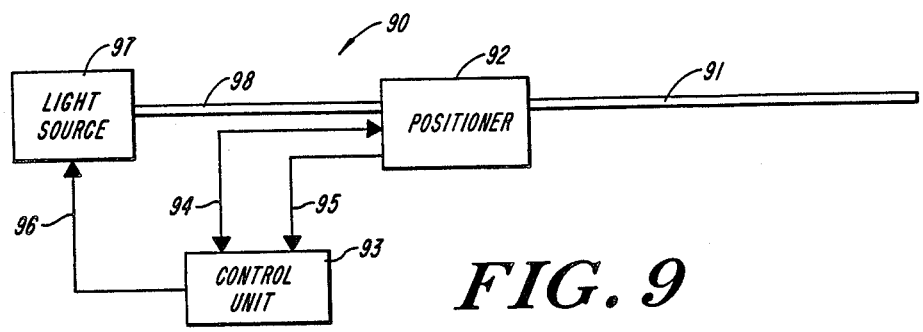
FIG. 9 is a block diagram of a probe and control system according to the invention.

FIG. 9 shows a schematic representation of such an embodiment 90 having a tip portion 91 containing a light conduit or fiber element and a lens relatively movable with respect to the fiber, and also having a positioner 92 included a handle structure with means for controllably moving the lens and/or fiber. A control unit 93 receives signals, which may be indicative of motor movement or handle position, along lines 94, 95 as control signals. Unit 93 may include a microprocessor to monitor or control the focus and the spot intensity of the probe. User-activated switches in the handle may provide selection signals over line 95 indicative of selected spot size. Line 94 carries control signals to the positioner, and may also carry position-indicating signals to the control unit. Responsive to selection signals on line 95, or position indicating signals on line 94, control unit 93 provides signals over line 96 to light source 97 to control the intensity of and/or to trigger the source.

The control means may be configured, e.g., to achieve constant power density independently of selected spot size. Alternatively, the handle portion 92 of the probe may include hand activated switches to provide signals indicative of the chosen spot size. Such signals are then sensed by the control unit to select the level of laser power supplied to the fiber, and to control the positioner so as to achieve a desired spot size and intensity. The control unit may also, responsive to a hand-switched signal on lines 94, 95, activate a low-power light source to permit the surgeon to visualize the output beam for positioning the probe at its working distance from the target tissue. Thus, for example, a "focus" button may be provided on the handle for this purpose, as well as a "trigger" button.

The invention having been thus described, further variations and improvements thereof will occur to those skilled in the art, and all such further variations and improvements are intended to be within the scope of the invention as defined by the following claims.

What is claimed is:

1. An ophthalmic endophotocoagulation probe for the application of light energy of a desired power to a target region of tissue within the eye of a subject, such probe comprising
    a handle
    a probe tip having an elongate hollow and substantially rigid outer body carried by said handle and extending from said handle to a distal light output end said outer body having a diameter and a length for insertion into the eye and manipulation therein by said handle
    a graded index convergent lens included in the light output end of said probe tip, said lens constituting a light transmissive window closing said outer body to provide a sealed enclosed region within said outer body, said graded index lens having a first end face facing outwardly of said enclosed region and defining an extreme extension of said probe tip and a second end face facing inwardly and defining an end wall of said enclosed region
    a light conducting fiber extending within said enclosed region to a light emitting fiber end,
    means included in said handle for causing relative motion of said fiber and said outer body to axially position said light emitting fiber end and said second end face at a spacing effective to project an output beam having a desired light energy in a defined region spaced from said first face for treating eye tissue.

2. A probe according to claim 1, wherein said means for causing relative motion comprises
    variable-positioning means for positioning said fiber end with respect to the convergent lens at any selected one of a plurality of desired fiber-lens spacings so as to attain any of one of a corresponding plurality of spot sizes, each said spot size being convergently formed in a focal region spaced from said light output end by a distance corresponding to a said fiber-lens spacing.

3. A probe according to claim 2, wherein the variable-positioning means comprises
    a first member carrying the optical fiber and having a stop structure operatively coupled thereto,
    a second member carrying the convergent lens, said second member being operatively interconnected with the first member and having a stop-engaging structure operatively coupled thereto, said stop structure and stop-engaging structure determining a plurality of offset positions of the first and second members thereby determining the plurality of desired fiber-lens spacings by relative movement of said first and second members.

4. A probe according to claim 2, wherein said variable-positioning means comprises a drive member mounted in said handle actuable by user manipulation directed parallel to the probe tip for effecting said positioning.

5. A probe according to claim 3, wherein said fiber and said lens are each carried by respective sheaths, said respective sheaths being mounted for telescoping motion one about the other, and wherein said variable-positioning means includes means for moving one said sheath with respect to the other said sheath.

6. A probe according to claim 2, wherein the variable-positioning means further comprises means for positioning said fiber end at a distance from the convergent lens effective to attain at least one of a collimated or a divergent output beam.

7. A laser endophotocoagulation probe for the application of light energy to eye tissue by the insertion of the probe within the eye, such probe comprising
    a handle
    a first tubular sheath extending from a handle and located at the handle to a distal tip end, said first tubular sheath being substantially rigid and defining a probe tip manipulable by said handle for insertion into the eye,
    a second tubular sheath having a first end portion coaxially carried within said first tubular sheath and extending to an output end within said first tubular sheath at a position proximate to the distal tip end, said first and second sheaths being axially movable relative to each other,
    an optical fiber mounted in said second tubular sheath and having a polished light output face located at said output end,
    a graded index convergent lens closing the distal tip end of said first tubular sheath and having an outer face defining an end of said probe tip and an inner face spaced from said output end,
    means in said handle operatively coupled to both said first and second sheaths for causing preselected axial motion of one sheath relative to another so that the light output face is spaced from the inner face of said graded index lens by a distance effective to project a convergent spot at a selected distance from said lens outer face for treatment of eye tissue.

8. A laser endophotocoagulation probe according to claim 7, wherein said means operatively coupled comprises first means for fixedly securing one said sheath with respect to the handle and a cam operatively coupled to move the other said sheath.

9. A laser endophotocoagulation probe according to claim 7, wherein at least one of said handle and said first tubular sheath is formed of a polymer.

10. A laser endophotocoagulation probe for the application of light energy of a desired power to a target region of tissue, such probe comprising
    A. a light conducting tip assembly having a housing insertable into an eye and including
        (i) an optical fiber having a first end portion for receiving light energy from a source, and a second end portion for emitting said received energy, and
        (ii) lens means for convergently focusing in a focal region thereof light from the second end portion, said lens means including a graded index lens said focal region being in operation aligned with the target region, B. handle means for moving the light conducting assembly within the eye so as to align the focal region with a desired target region, and C. variable-positioning means for positioning said second end portion at any selected one of a plurality of desired spacings with respect to the lens means to attain any one of a corresponding plurality of spot sizes, each said spot size being convergently formed in a different focal region, such variable positioning means including (i) a first threaded member carrying the optical fiber and having a stop member thereon, and (ii) a second member carrying the lens means, said second member being threadedly mated with the first member and having a stop-engaging member thereon, said stop member and stop-engaging member determining a plurality of rotationally offset positions of the first and second members thereby achieving the plurality of desired spacings of the second end portion and lens means by relative rotation of said first and second members.

* * * * *